(12) United States Patent
Asleson et al.

(10) Patent No.: US 10,806,922 B2
(45) Date of Patent: Oct. 20, 2020

(54) MEDICAL ACCESS TOOLS, ASSEMBLIES, AND METHODS

(71) Applicant: Medtronic, Inc., Minneapolis, MN (US)

(72) Inventors: Andrea J. Asleson, Maple Grove, MN (US); Ronald A. Drake, St. Louis Park, MN (US); Mark T. Marshall, Forest Lake, MN (US); Kelly M. Wien, Big Lake, MN (US)

(73) Assignee: Medtronic, Inc, Minneapolis, MN (US)

( * ) Notice: Subject to any disclaimer, the term of this patent is extended or adjusted under 35 U.S.C. 154(b) by 486 days.

(21) Appl. No.: 14/620,410

(22) Filed: Feb. 12, 2015

(65) Prior Publication Data

US 2016/0235973 A1 Aug. 18, 2016

(51) Int. Cl.
*A61N 1/05* (2006.01)
*A61B 17/34* (2006.01)

(52) U.S. Cl.
CPC ........ *A61N 1/0592* (2013.01); *A61B 17/3478* (2013.01); *A61B 17/3468* (2013.01); *A61B 2017/349* (2013.01)

(58) Field of Classification Search
CPC ................ A61B 17/3468; A61B 17/34; A61B 2017/06076; A61B 2017/348; A61B 2017/3482; A61B 2017/3492
See application file for complete search history.

(56) References Cited

U.S. PATENT DOCUMENTS

| | | | |
|---|---|---|---|
| 4,884,567 A | 12/1989 | Elliott et al. | |
| 5,423,846 A | 6/1995 | Fischell | |
| 5,507,743 A * | 4/1996 | Edwards | A61N 5/045 |
| | | | 600/373 |
| 6,416,510 B1 | 7/2002 | Altman et al. | |
| 6,620,139 B1 * | 9/2003 | Plicchi | A61B 18/1477 |
| | | | 604/103.1 |
| 6,626,917 B1 * | 9/2003 | Craig | A61B 17/0401 |
| | | | 606/144 |
| 6,931,286 B2 | 8/2005 | Sigg et al. | |
| 7,103,418 B2 | 9/2006 | Laske et al. | |
| 8,628,552 B2 | 1/2014 | Toy et al. | |
| 8,690,819 B2 * | 4/2014 | Nita | A61B 17/22012 |
| | | | 604/22 |

(Continued)

FOREIGN PATENT DOCUMENTS

WO 2009006531 A1 1/2009

*Primary Examiner* — Christopher L Templeton

(57) ABSTRACT

A medical access tool includes a needle member extending along a longitudinal axis, and a coiled wire extending around the axis. An inner surface of the coiled wire, along a proximal segment thereof, is spaced radially apart from an outer surface of the needle member, and a distal segment of the coiled wire extends distally to a tissue-engaging tip of the coiled wire, a piercing distal tip of the needle member being recessed proximally from the tissue-engaging tip at a fixed distance. An operator may rotate the coiled wire to engage tissue, for example, that of a pericardial sac or a diaphragmatic attachment, which then travels proximally along the coiled wire and into contact with the needle member's distal tip, to be pierced through thereby. At least one lumen of the needle member provides a passageway through which the operator may advance a guide wire and/or inject a fluid.

7 Claims, 7 Drawing Sheets

(56) References Cited

U.S. PATENT DOCUMENTS

| | | |
|---|---|---|
| 8,801,665 B2 | 8/2014 | Sabbah |
| 2004/0002699 A1* | 1/2004 | Ryan ................. A61B 17/06066 606/27 |
| 2004/0068299 A1* | 4/2004 | Laske ................. A61M 25/0082 607/3 |
| 2004/0167546 A1* | 8/2004 | Saadat ............. A61B 17/00234 606/144 |
| 2004/0193217 A1* | 9/2004 | Lubbers ............. A61B 17/0401 606/232 |
| 2005/0149097 A1 | 7/2005 | Regnell et al. |
| 2006/0036265 A1* | 2/2006 | Dant ................. A61B 17/0469 606/144 |
| 2008/0108950 A1* | 5/2008 | Rioux ................. A61B 17/064 604/181 |
| 2008/0234717 A1 | 9/2008 | Bruszewski |
| 2008/0269763 A1 | 10/2008 | Bonde et al. |
| 2008/0294174 A1* | 11/2008 | Bardsley ............ A61B 17/3415 606/108 |
| 2009/0163862 A1* | 6/2009 | Kauphusman ........ A61M 25/04 604/117 |
| 2009/0240264 A1* | 9/2009 | Tuval ................. A61B 17/0469 606/148 |
| 2009/0254095 A1 | 10/2009 | Levine et al. |
| 2009/0259212 A1* | 10/2009 | Sabbah ............. A61M 25/0084 604/511 |
| 2012/0035654 A1* | 2/2012 | Belson ................. A61B 90/03 606/232 |
| 2012/0116418 A1* | 5/2012 | Belson ............... A61B 17/0469 606/139 |
| 2012/0123461 A1* | 5/2012 | Gillies ............... A61B 17/3423 606/185 |
| 2012/0136200 A1* | 5/2012 | Miraki ............... A61B 17/3423 600/37 |
| 2013/0178845 A1* | 7/2013 | Smith .................... A61B 18/18 606/33 |
| 2014/0148786 A1* | 5/2014 | Milo ................. A61B 17/3468 604/507 |
| 2014/0277056 A1* | 9/2014 | Poore ................. A61B 17/0218 606/190 |
| 2015/0190173 A1* | 7/2015 | Hiernaux ......... A61B 17/06066 606/185 |

* cited by examiner

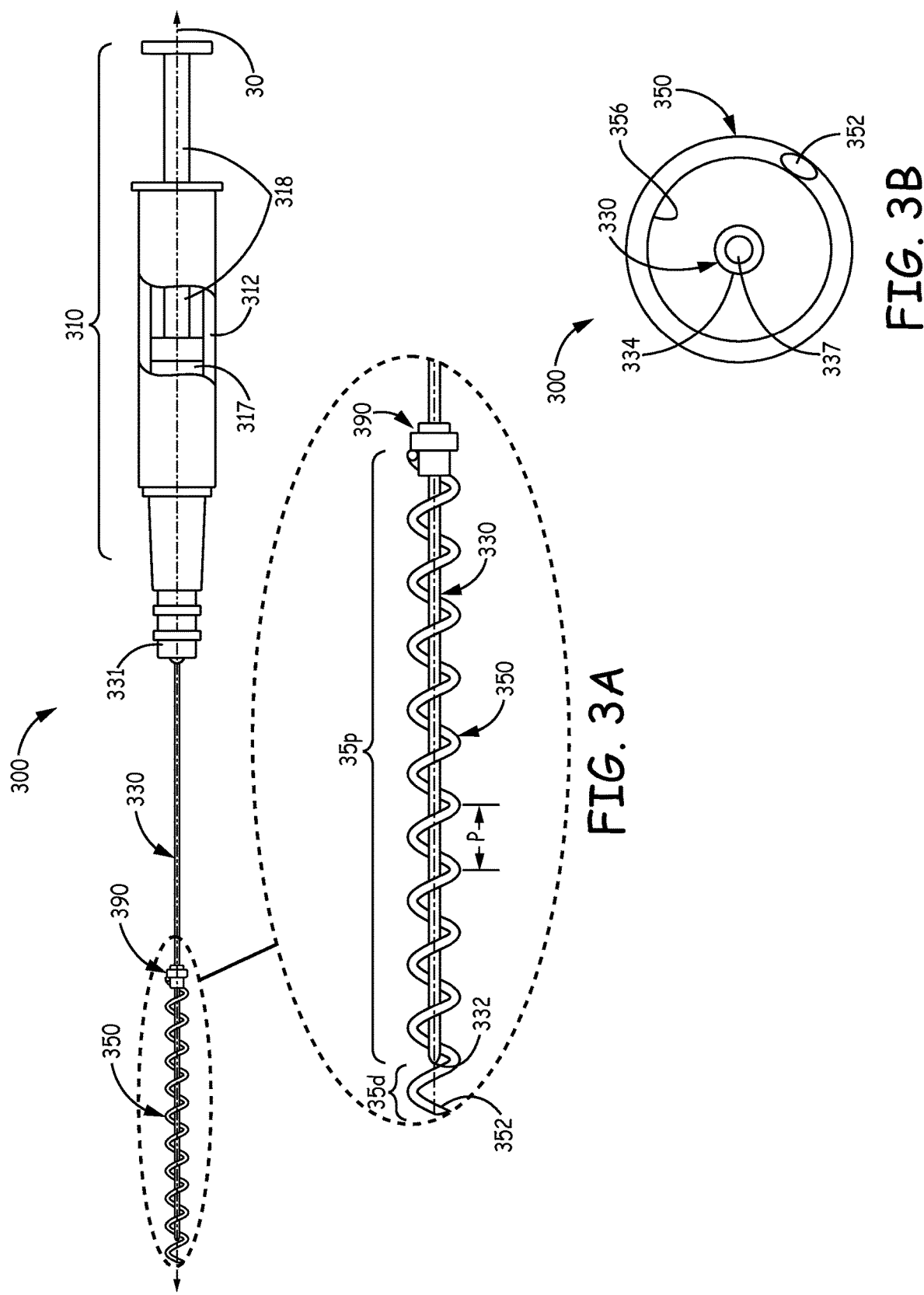

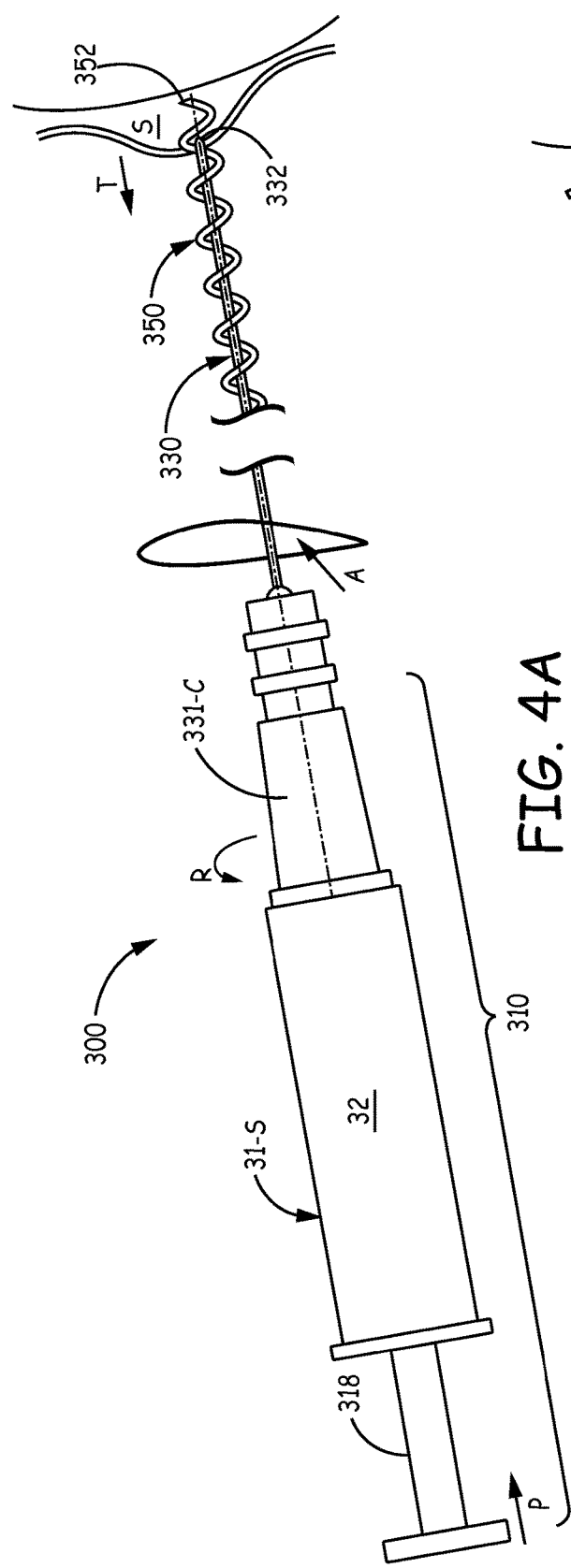
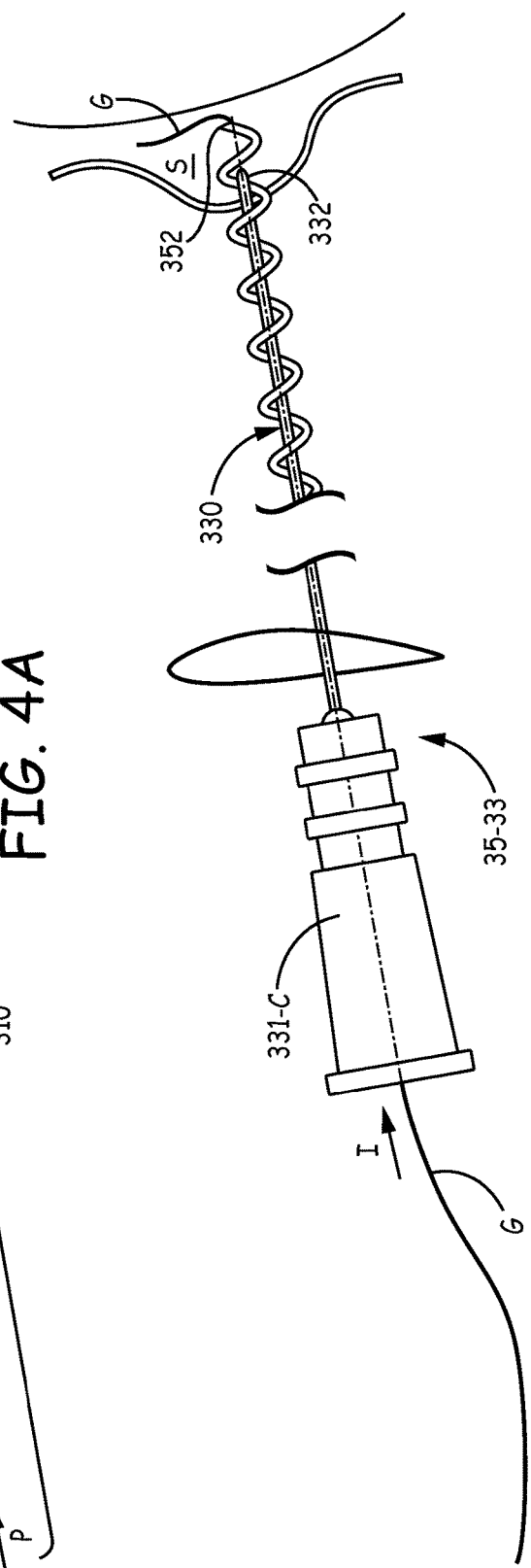
FIG. 4A
FIG. 4B

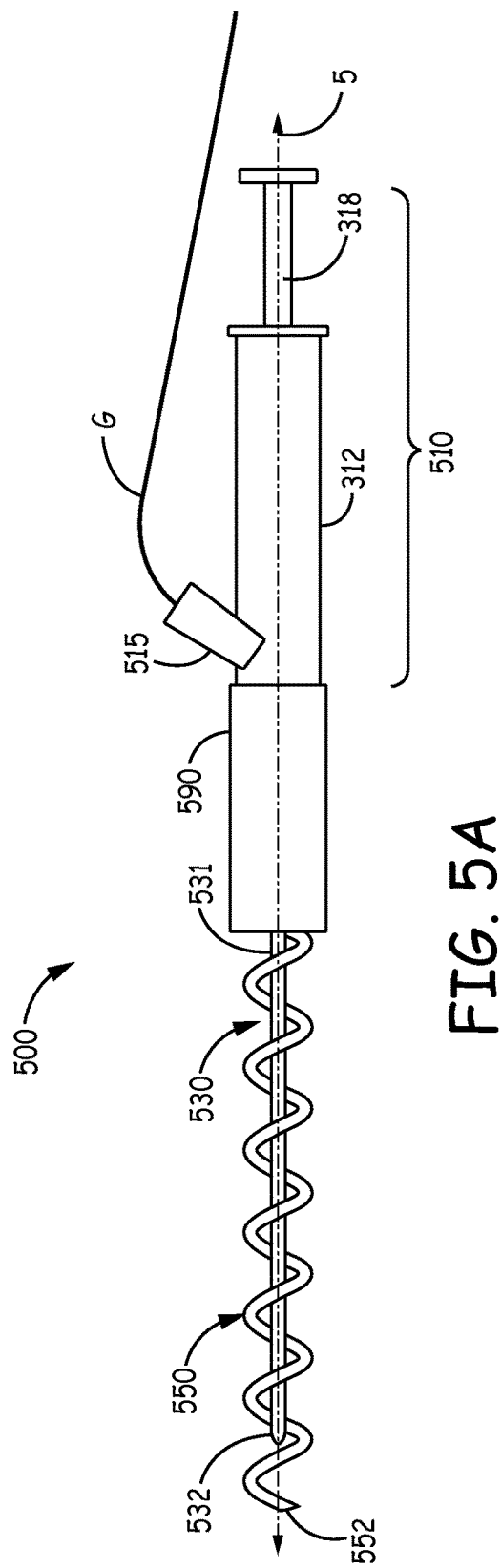
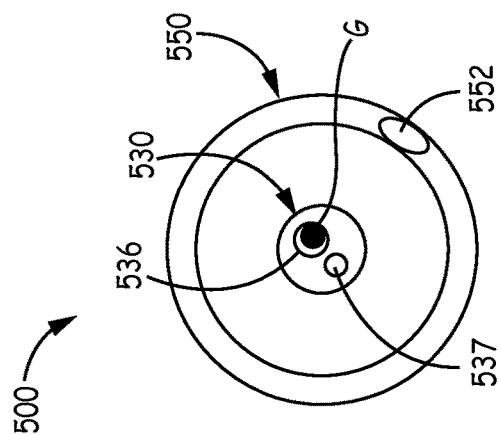

MEDICAL ACCESS TOOLS, ASSEMBLIES, AND METHODS

TECHNICAL FIELD

The present disclosure pertains to gaining access to extravascular spaces, for example, for the delivery of medical devices thereto, and more particularly to tools, assemblies thereof, and associated methods that are suitable for gaining access into a sub-sternal space or a space within the pericardial sac.

BACKGROUND

Implantable medical electrical leads, included in systems that are known in the art for delivering cardiac therapy and/or for providing cardiac monitoring, are often implanted transvenously within a heart of a patient. But extravascular implant sites may be preferred, for example, in those patients where vascular access is difficult, or because transvenous leads can become fibrosed in the heart over time, which makes lead revision and extraction procedures challenging.

SUMMARY

Embodiments and methods of the present disclosure enable an operator to gain access to certain extravascular spaces in a controlled fashion that mitigates the risk of perforating bodily organs. According to some embodiments, a medical access tool includes a needle member extending distally from a hub of the tool, along a longitudinal axis of the tool, and a coiled wire extending around the longitudinal axis of the tool with an open pitch. An inner surface of the coiled wire, along a proximal segment thereof, is spaced radially apart from an outer surface of the needle member, and a distal segment of the coiled wire extends distally from the proximal segment to a tissue-engaging tip thereof, a piercing distal tip of the needle member being recessed proximally from the tissue-engaging tip. When the operator has positioned the tissue-engaging tip of the coiled wire in close proximity to a diaphragmatic attachment or a pericardial sac and rotates the coiled wire to engage either, the tissue thereof rides, or travels along the turns of the coiled wire and into engagement with the piercing distal tip of the needle member to be pierced therethrough in a controlled fashion. Once the distal tip of the needle has pierced through the tissue of either the diaphragmatic attachment or the pericardial sac, a lumen of the needle member provides a passageway through which the operator may advance a guide wire into the sub-sternal space or the space within the pericardial sac.

A distance at which the distal tip of the needle member is recessed from the tissue-engaging tip of the coiled wire is preferably fixed during the operation of the tool, because a junction that secures the coiled wire to the needle member and/or to the hub is configured to prevent movement of the coiled wire along the longitudinal axis of the tool relative to the needle member, and because a stiffness of the coiled wire is such that the pitch of the coiled wire does not significantly deform during operation. According to some embodiments, a sidewall of the tool hub defines a cavity, and the hub includes an injection member operably coupled to the cavity, wherein the cavity, which contains an injection fluid, is in fluid communication with a lumen of the needle member so that, according to some methods of the present invention, the operator can inject the fluid from the cavity through the lumen of the needle while rotating the coiled wire. The hub of the tool, in some embodiments, further includes a connector and may be in the form of a syringe assembly, wherein the needle member proximal end is configured to engage with, and disengage from the connector. Thus, the needle member and the coiled wire may together form an assembly that can be separated from the hub.

BRIEF DESCRIPTION OF THE DRAWINGS

The following drawings are illustrative of particular exemplary embodiments and do not limit the scope of the invention. The drawings are not to scale (unless so stated) and are intended for use in conjunction with the explanations in the following detailed description. Embodiments will hereinafter be described in conjunction with the appended drawings wherein like numerals denote like elements.

FIGS. 3A-B are a plan view and an end view of a medical access tool, according to some embodiments;

FIGS. 4A-B are schematics outlining methods of the present invention; and

FIGS. 5A-B are a plan view and an end view of a medical access tool, according to some alternate embodiments.

DETAILED DESCRIPTION

The following detailed description is exemplary in nature and is not intended to limit the scope, applicability, or configuration of the invention in any way. Rather, the following description provides practical examples, and those skilled in the art will recognize that some of the examples may have suitable alternatives.

Figure 1A:
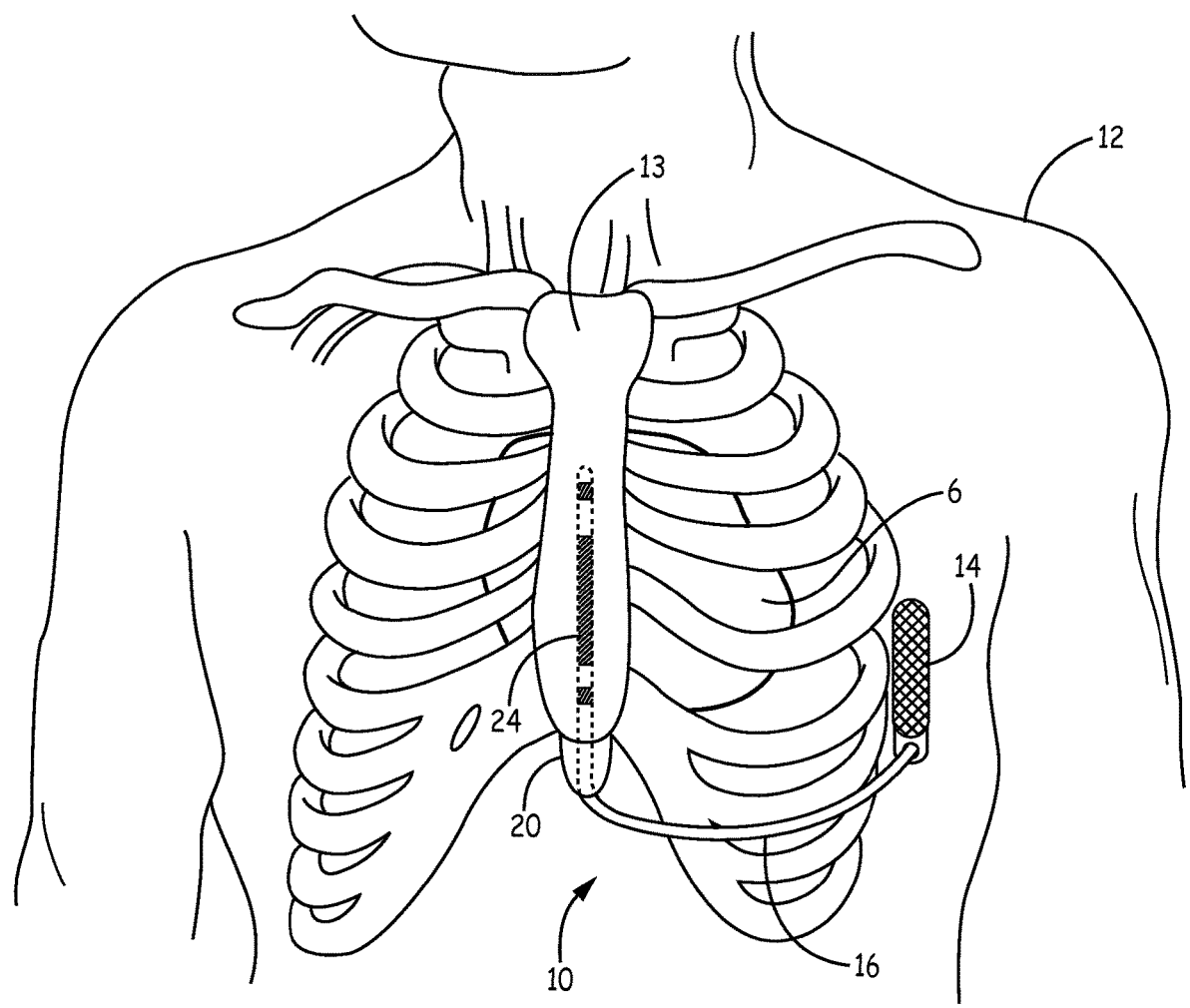
FIGS. 1A-B are schematics showing an exemplary extravascular implant.
Figure 1B:
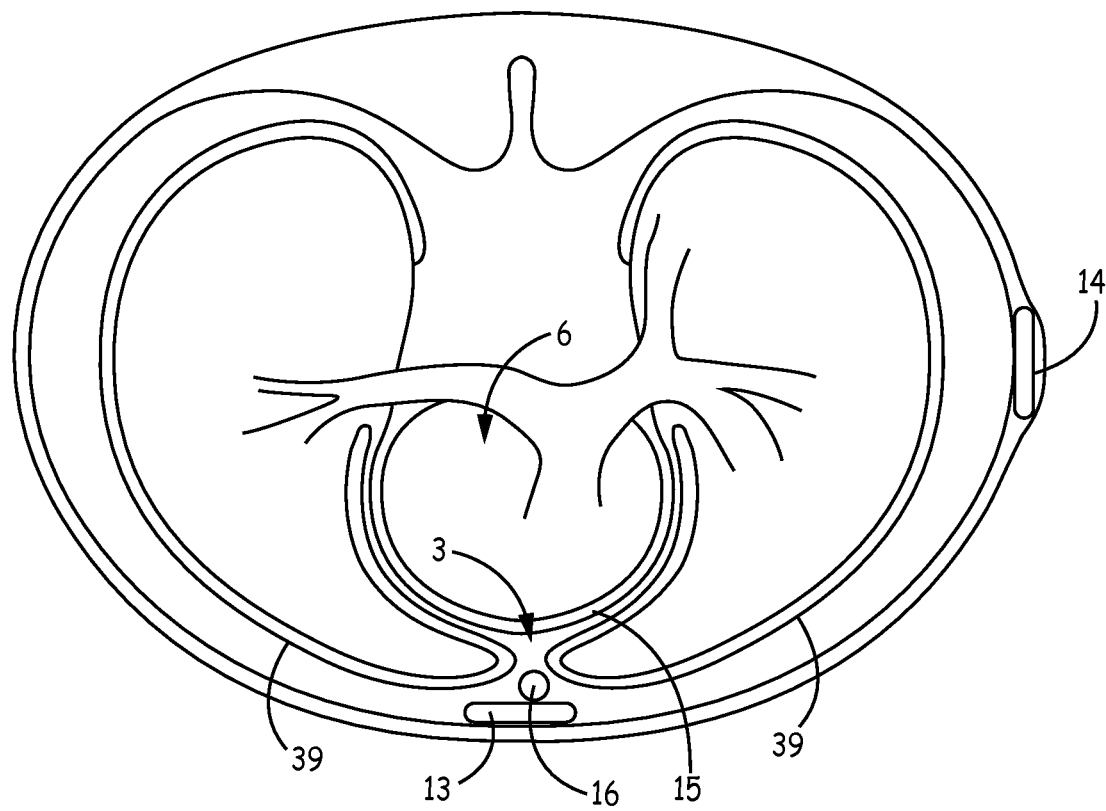

FIGS. 1A-B are schematics showing an exemplary extravascular implant of an exemplary system 10 that includes a pulse generator device 14 and an implantable medical electrical lead 16 coupled thereto. Device 14 is shown implanted subcutaneously on the left mid-axillary of a patient 12, superficially of the patient's ribcage. Device 14, for example, which may be configured to provide cardiac defibrillation therapy, includes a hermetically sealed housing in which the appropriate electronics and a power supply are contained, and which is formed from a conductive material, such as titanium, or from a combination of conductive and non-conductive materials. Device 14 further includes a connector module by which lead 16 is electrically coupled to the electronics contained therein, for example, by electrical contacts contained within the module and a corresponding hermetically sealed feedthrough assembly, such as is known in the art. The conductive material of device housing may be employed as an electrode, for example, to provide the aforementioned therapy in conjunction with a defibrillation electrode 24 of lead 16, which is shown at least partially implanted in a sub-sternal space of the anterior mediastinum 3, for example, within the loose connective tissue and/or sub-sternal musculature thereof. With reference to FIG. 1B, the anterior mediastinum 3 may be viewed as being bounded laterally by pleurae 39 that enclose the patient's lungs, posteriorly by the pericardial sac 15 that encloses the patient's heart 6, and anteriorly by the sternum 13. In some instances, the anterior wall of the anterior mediastinum 3 may also be formed by the transversus thoracis and one or more costal cartilages. With further reference to FIG. 1B, an alternative extravascular implant site for a medical electrical lead, such as lead 16, may be along an epicardial surface of heart 6, within the space enclosed by the pericardial sac 15.

Figure 2:
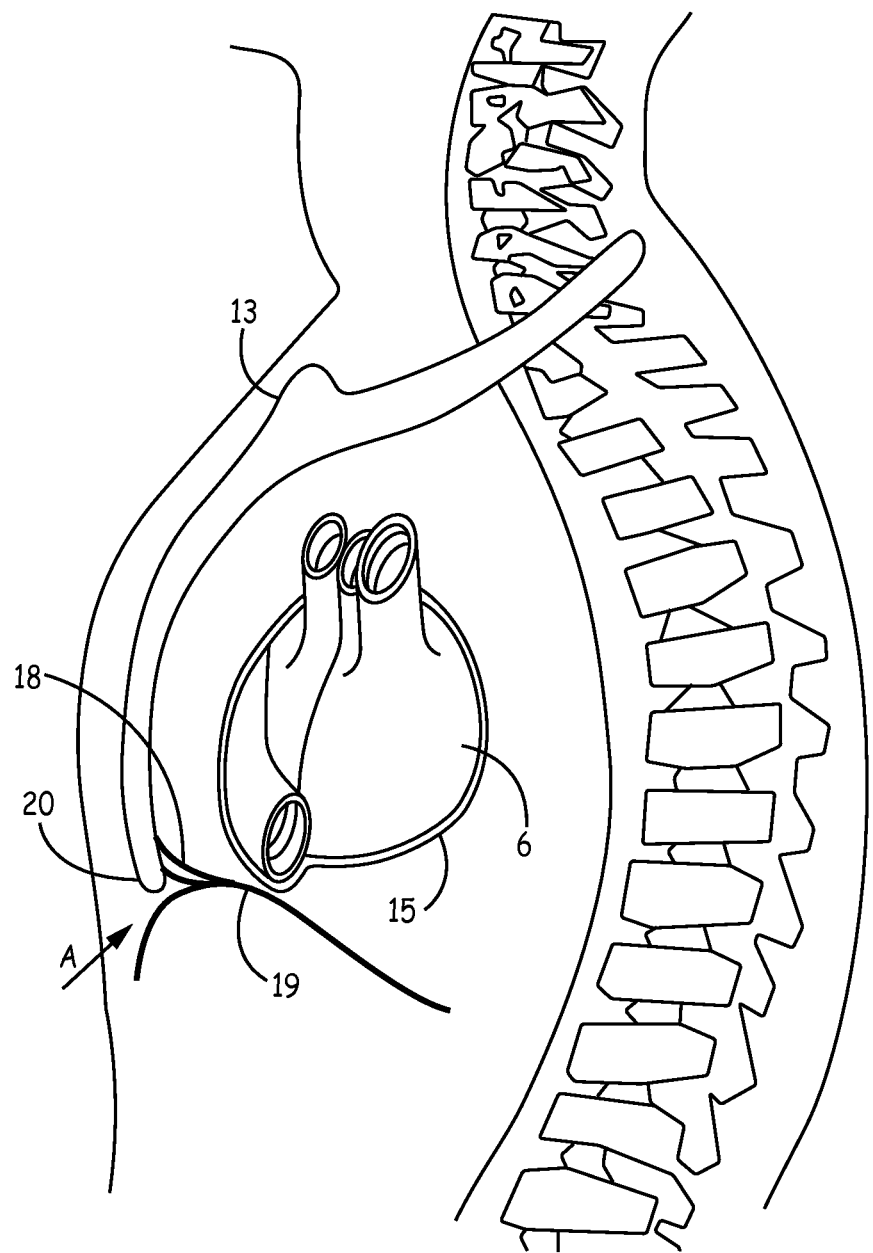
FIG. 2 is a schematic for describing sub-sternal access for extravascular implants.

FIG. 2 is a schematic showing an access site A for creating a passageway between a patient's diaphragm 19 and xiphoid process 20 of sternum 13, for example, to implant a medical electrical lead within a sub-sternal space of the anterior mediastinum 3 (FIG. 1B), or within the pericardial sac 15. After making a superficial incision, an operator may open a passageway between diaphragmatic attachments 18 and diaphragm 19 by using blunt dissection tools and techniques that are known in the art; alternately the operator may use a percutaneous approach. In either case, in some instances, the operator may need to employ a piercing tool to pass through the diaphragmatic attachments 18 or the pericardial sac 15, depending on the desired implant location. Embodiments and methods disclosed herein provide for a controlled piercing through either of the aforementioned tissues in order to reduce the risk of puncturing the heart 6 within the pericardial sac 15, and/or the pleurae 39, or other structures within the anterior mediastinum 3, such as lymph vessels, lymph glands, branches of the internal thoracic artery, the internal thoracic vein, etc.

FIGS. 3A-B are a plan view and an end view of a medical access tool 300, according to some embodiments. FIG. 3A illustrates tool 300 including a hub 310, a needle member 330 secured to hub 310 at a proximal end 331 thereof, and a coiled wire 350 extending with an open pitch around a longitudinal axis 30 of tool 300. FIG. 3A further illustrates hub 310 including a sidewall 312 defining a cavity 317, and an injection member 318 operably coupled to cavity 317 to inject fluid therefrom and through a lumen 337 of needle member 330, which is in fluid communication with cavity 317 and can be seen in the end view of FIG. 3B. (Note that the FIG. 3B end view shows only coiled wire 350 and needle member 330 for the sake of clarity in illustration.) According to the illustrated embodiment, lumen 337 of needle member 330 extends along longitudinal axis 30 of tool 300, from a proximal opening thereof at proximal end 331 to a distal opening thereof at a piercing distal tip 332 of needle member 330, which is best seen in the enlarged detail of FIG. 3A.

With further reference to FIG. 3A, coiled wire 350 includes a proximal segment 35$p$, a distal segment 35$d$, and a tissue-engaging tip 352. Distal segment 35$d$ is shown extending from proximal segment 35$p$ to tissue-engaging tip 352, and piercing distal tip 332 of needle member 330 is recessed from tissue-engaging tip 352 by a distance equal to a length of distal segment 35$d$. FIGS. 3A-B further illustrate an inner surface 356 of coiled wire 350 being spaced radially apart from an outer surface 334 of needle member 330 along a length of proximal segment 35$p$. FIG. 3A shows a junction 390 securing coiled wire 350 to needle member 330, and, according to preferred embodiments, junction 390 is configured to prevent movement of coiled wire 350 along longitudinal axis 30, relative to needle member 330. Furthermore, coiled wire 350 preferably has a stiffness that prevents significant deformation thereof during the operation of tool 300, which will be described below. Thus, the distance at which piercing distal tip 332 of needle member 330 is recessed from tissue-engaging tip 352 of coiled wire 350 is fixed.

According to some exemplary embodiments, needle member 330 is formed from a medical grade stainless steel, has an outer diameter of between approximately 0.05 and 0.1 inch, and a lumen diameter of approximately 0.04 inch. Coiled wire 350 may have an outer diameter between approximately 0.1 inch and approximately 0.3 inch, and be formed from a medical grade stainless steel wire that has a diameter of approximately 0.03 inch, for example, if tool 300 is intended for passing through pericardial sac 15. If tool 300 is intended for passing through diaphragmatic attachments 18, the diameter of wire forming coiled wire 350 may be larger, for example, approximately 0.063 inch, and the outer diameter of coiled wire 350 may be approximately 0.36 inch. Likewise, when needle member 330 is employed in embodiments of tool 300 that are intended for passing through diaphragmatic attachments 18, needle member 330 has a larger outer diameter, for example, approximately 0.19 inch, with a lumen diameter of approximately 0.15 inch. With further reference to FIG. 3A, for either intended use, a pitch length P of coiled wire 350 may be approximately 0.15 inch, wherein the length of distal segment 35$d$ may be approximately one turn, or pitch length P, and a length of proximal segment 35$p$ may be between approximately 0.2 inch and approximately 0.5 inch. A junction 390 between coiled wire 350 and needle member 330 may be formed by laser welding, for example, by welding each to an interfacing weld collar as depicted in FIG. 3A. It should be noted that the above dimensions and weld junction are exemplary in nature, as stated, and should not be considered limiting of embodiments described herein.

Figure 3C:
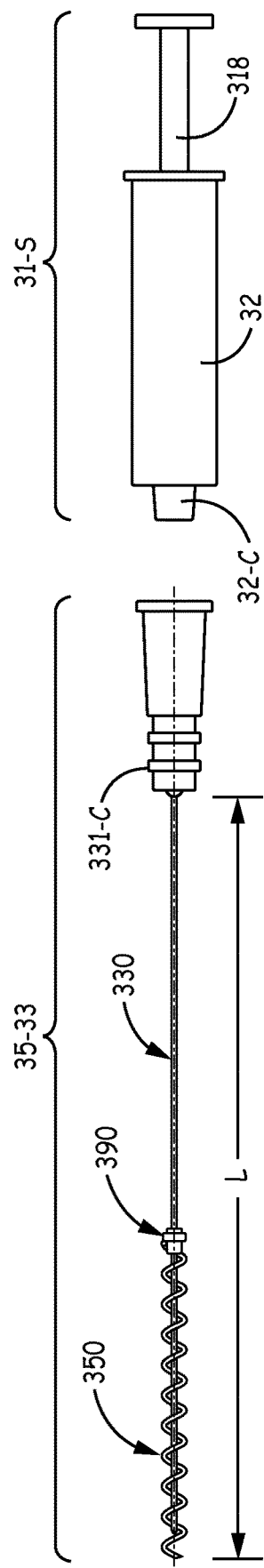
FIG. 3C is a plan view of portions of the tool separated from one another, according to some embodiments.

FIG. 3C is a plan view of portions of tool 300 separated from one another, according to some embodiments. FIG. 3C illustrates an assembly 35-33 of needle member 330 and coiled wire 350, in which a proximal end 331-C of needle member 330 is configured to engage with, and disengage from a connector 32-C of a syringe assembly 31-S, which corresponds to hub 310. Proximal end 331-C may simply form a press fit around connector 32-C for engagement therewith, or may include luer lock features, known in the art, to mate with a luer lock fitting of connector 32-C (not shown). Although not shown, it should be understood that the proximal opening of lumen 337 of needle member 330 (FIG. 3B) is defined by proximal end 331-C, and that a barrel 32 of syringe assembly 31-S has an interior similar to cavity 317 shown in FIG. 3A, in which injection member 318 is operably engaged, and which is in fluid communication with lumen 337 (via an opening in connector 32-C), when proximal end 331-C is engaged with connector 32-C. In either embodiment of tool 300, proximal end 331/331-C of needle member 330 may be formed from any suitable hard plastic, as may hub 310/connector 32-C and barrel 32 of syringe assembly 31-C, and injection member 318 may be constructed according to any suitable plunger design known in the art for injecting fluid from cavity 317/interior of barrel 32 and through the needle member lumen. It should be noted that, according to some alternate embodiments, needle member 330 may be used alone as a tool, wherein proximal end 331-C functions as a handle.

FIGS. 4A-B are schematics outlining methods of the present invention, in which tool 300 is used to gain access into a sub-sternal space S, or a space within a pericardial sac S, depending upon the intended implant site. FIG. 4A shows tool 300 having been advanced by an operator through an incision at an access site, for example, access site A that was described above in conjunction with FIG. 2. Although not shown, an introducer sheath, commonly employed by operators skilled in the art, may have been positioned by the operator within the access site A to provide a passageway for the insertion of tool 300, for example, when taking a percutaneous approach, as opposed to the aforementioned blunt dissection of a surgical approach. With reference back to FIG. 3A a length L of tool 300, generally defined between proximal end 331-C (or proximal end 331 of the embodiment shown in FIG. 3A) and tissue-engaging tip 352 of coiled wire 350, may be as short as approximately 0.5 inch, if the surgical approach is used, but may need to be as long as approximately 5 inches, if the percutaneous approach is taken.

Once the operator brings tissue-engaging tip 352 into contact with the diaphragmatic attachment or pericardial sac (depending on the intended implant site), the operator, without advancing tool 300 any further, rotates tool 300, per arrow R of FIG. 4A. The resulting rotation of coiled wire 350 and causes tissue-engaging tip 352 thereof to engage with the diaphragmatic attachment or pericardial sac (depending on the intended implant site), so that the tissue thereof travels proximally along the helical path of coiled wire 350, per arrow T, and into contact with piercing distal tip 332 of needle member 330. The nature of the tissue, for example, being a relatively thin wall, along with the aforementioned stiffness of coiled wire 350, which does not allow significant deformation thereof, allow the rotation of engaged coiled wire 350 to pull the tissue along the turns thereof and away from an underlying tissue bulk as illustrated in FIGS. 4A-B. Thus, as long as the operator does not advance tool 300 while rotating tool 300, the risk of perforating the underlying bulk of tissue with tip 352 of coiled wire 350 is mitigated. FIG. 4B shows coiled wire 350 having been rotated enough so that the tissue has traveled along at least one turn thereof to be pierced through by piercing distal tip 332 of needle member 330. Thus, the tissue may be said to be passively pierced through by distal tip 332 in a relatively controlled fashion, having been brought into engagement therewith by the rotation of coiled wire 350, as opposed to being pierced through by applying a push force to needle member 330 that may be difficult to control in preventing tip 332 from perforating an organ or other sub-sternal structure after piercing through the tissue of the diaphragmatic attachment or pericardial sac. According to some methods, the operator may inject radiopaque fluid from piercing tip 332 of needle member 330 (e.g., through needle member lumen 337 and out the distal opening thereof), for example, by activating injection member 310, for example, per arrow P, in the midst of rotating tool 300 to engage tissue-engaging tip 352, wherein the operator monitors the dispersion of injected fluid from tip 332 to determine when piercing distal tip 332 has pierced through the tissue of the diaphragmatic attachment or pericardial sac.

FIG. 4B further illustrates tool 300 conforming to the embodiment that allows for separation of assembly 35-33 from syringe assembly 31-S, for example, after the tissue has been pierced through by needle member tip 332. According to FIG. 4B, this separation allows insertion, per arrow I, of a guide wire G into space S, through the proximal opening of the needle member lumen, formed by proximal end 331-C, and out through the distal opening of the lumen at distal tip 332, so that guide wire G can provide access to space S. After the operator removes assembly 35-33 from over the positioned guide wire G, the operator can advance an implantable medical device, for example, a lead like implantable medical electrical lead 16 described above, over guide wire G and through access site A into space S. Guide wire G may be constructed according to the types known in the art of interventional cardiology, and, according to an exemplary embodiment, may have a diameter of approximately 0.035 inch.

FIGS. 5A-B are a plan view and an end view of a medical access tool 500, according to some alternate embodiments. FIG. 5A illustrates tool 500 including a hub 510, a needle member 530, a coiled wire 550, and a junction 590 formed as a collar that secures coiled wire 550 to hub 510. Coiled wire 550 is shown extending with an open pitch around a longitudinal axis 5 of tool 500, wherein the collar of junction 590 may be insert molded around a proximal end of coiled wire 550 and coupled to hub 510 by any suitable type of bond or mechanical interlock known in the art, wherein the coupling may allow for rotation of coiled wire 550 relative to needle member 530, in some embodiments as mentioned below. FIG. 5B illustrates needle member 530 including a pair of lumens 536, 537, each of which extend from distal openings, at a piercing distal tip 532 of needle member 530, to proximal openings, at a proximal end of needle member 530. (Note that the FIG. 5B end view shows only coiled wire 550 and needle member 530 for the sake of clarity in illustration.) According to the illustrated embodiment, needle member 530 extends within the collar of junction 590 to the proximal end thereof (not shown), which is secured to hub 510 so that lumen 536 is in fluid communication with a guide wire entry port 515 of hub 510, to allow passage of guide wire G therethrough, and so that lumen 537 is in fluid communication with a cavity of hub 510, which is similar to cavity 317 of hub 310 (FIG. 3A), being defined by sidewall 312 and operably coupled with injection member 318. According to some exemplary embodiments, each of lumens 536, 537 have a diameter of approximately 0.04 inch.

With further reference to FIGS. 5A-B, an inner surface of coiled wire 550 is spaced radially apart from an outer surface of needle member 530, and distal piercing tip 532 of needle member 530 is recessed proximally from a tissue-engaging tip 552 of coiled wire 550, such that the operator may employ access tool 500 in generally the same fashion as was described above for access tool 300, to pierce through tissue of the diaphragmatic attachment or pericardial sac by rotating coiled wire 550. Coiled wire 550, like coiled wire 350 of tool 300, preferably has a stiffness that prevents significant deformation thereof during the operation of tool 500, and is preferably constrained by junction 590 from moving longitudinally along axis 5, relative to needle member 530. Because tool 500 includes entry port 515 and lumen 536 for the passage of guide wire G, hub 510 need not be separated from needle member 530 and coiled wire 550 in order to advance guide wire G through lumen 536, which allows the operator to employ guide wire G prior to, or intermittently with injection member 318 during the operation of tool 500, for example, probing with guide wire G prior to, or in the midst of rotating coiled wire 350 while monitoring the dispersion of injected radiopaque fluid. Furthermore, according to some embodiments, junction 590 is configured to allow rotation of coiled wire 550 relative to needle member 530, which may be desirable when the operator employs guide wire G intermittently with injection member 318, for example, in the midst of rotating coiled wire 550 to engage tissue of the diaphragmatic attachment or pericardial sac.

In the foregoing detailed description, the invention has been described with reference to specific embodiments. However, it may be appreciated that various modifications and changes can be made without departing from the scope of the invention as set forth in the appended claims.

The invention claimed is:
1. A medical access tool comprising:
   a needle member including a proximal end, a piercing distal tip, and a lumen, the needle member extending along a longitudinal axis of the medical access tool between the proximal end thereof and the piercing distal tip thereof, the lumen extending from a proximal opening thereof at the proximal end to a distal opening thereof at the distal tip;

a coiled wire extending around the longitudinal axis of the medical access tool with a pitch, the coiled wire including a proximal segment, a distal segment, and a tissue-engaging tip, the coiled wire having an inner surface, the inner surface being spaced radially apart from an outer surface of the needle member along a length of the proximal segment, the distal segment extending distally from the proximal segment to the tissue-engaging tip, the distal tip of the needle member being recessed proximally from the tissue-engaging tip by a fixed distance equal to a length of the distal segment, and the coiled wire having a stiffness that prevents significant deformation of the pitch thereof during operation of the medical access tool, wherein the coiled wire is configured to proximally pull tissue up the coiled wire by rotating without advancing until the distal tip passively pierces the tissue without advancing:

a junction connecting the coiled wire to the medical access tool, the junction being configured to prevent movement of the coiled wire along the longitudinal axis of the medical access tool relative to the needle member; and a hub at a proximal portion of the medical access tool that is secured to the proximal end of the needle member, the hub including a sidewall defining a cavity, and an injection member operably coupled to the cavity, the cavity being configured to contain an injection fluid, and the cavity being in fluid communication with the lumen of the needle member;

wherein the junction connecting the coiled wire comprises a collar mounted around the hub.

2. The medical access tool of claim 1, wherein the junction is further configured to allow rotation of the coiled wire relative to the needle member.

3. A medical access tool comprising:

a needle member including a proximal end, a piercing distal tip, and a lumen, the needle member extending along a longitudinal axis of the medical access tool between the proximal end thereof and the piercing distal tip thereof, the lumen extending from a proximal opening thereof at the proximal end to a distal opening thereof at the distal tip;

a coiled wire extending around the longitudinal axis of the medical access tool with a pitch, the coiled wire including a proximal segment, a distal segment, and a tissue-engaging tip, the coiled wire having an inner surface, the inner surface being spaced radially apart from an outer surface of the needle member along a length of the proximal segment, the distal segment extending distally from the proximal segment to the tissue-engaging tip, the distal tip of the needle member being recessed proximally from the tissue-engaging tip by a fixed distance equal to a length of the distal segment, and the coiled wire having a stiffness that prevents significant deformation of the pitch thereof during operation of the medical access tool, wherein the coiled wire is configured to proximally pull tissue up the coiled wire by rotating without advancing until the distal tip passively pierces the tissue without advancing: and a junction connecting the coiled wire to the medical access tool, the function being configured to prevent movement of the coiled wire along the longitudinal axis of the medical access tool relative to the needle member;

wherein the length of the distal segment of the coiled wire is approximately 0.15 inch, and the coiled wire completes a full revolution along the distal segment.

4. A medical access tool comprising:

a needle member including a proximal end, a piercing distal tip, and a lumen, the needle member extending along a longitudinal axis of the medical access tool between the proximal end thereof and the piercing distal tip thereof, the lumen extending from a proximal opening thereof at the proximal end to a distal opening thereof at the distal tip;

a coiled wire extending around the longitudinal axis of the medical access tool with a pitch, the coiled wire including a proximal segment, a distal segment, and a tissue-engaging tip, the coiled wire having an inner surface, the inner surface being spaced radially apart from an outer surface of the needle member along a length of the proximal segment, the distal segment extending distally from the proximal segment to the tissue-engaging tip, the distal tip of the needle member being recessed proximally from the tissue-engaging tip by a fixed distance equal to a length of the distal segment, and the coiled wire having a stiffness that prevents significant deformation of the pitch thereof during operation of the medical access tool, wherein the coiled wire is configured to proximally pull tissue up the coiled wire by rotating without advancing until the distal tip passively pierces the tissue without advancing; and a junction connecting the coiled wire to the medical access tool the junction being configured to prevent movement of the coiled wire along the longitudinal axis of the medical access tool relative to the needle member;

wherein the junction connecting the coiled wire comprises a collar mounted around the needle member.

5. An assembly for a medical access tool, the assembly comprising:

a needle member including a proximal end, a piercing distal tip, and a lumen, the needle member extending along a longitudinal axis of the assembly between the proximal end thereof and the piercing distal tip thereof, the lumen extending from a proximal opening thereof at the proximal end to a distal opening thereof at the distal tip, the proximal end being configured to engage with, and disengage from a connector of a syringe assembly, such that the lumen is in fluid communication with an interior of a barrel of the syringe assembly, when the proximal end is engaged therewith;

a coiled wire extending around the longitudinal axis of the assembly with a pitch, the coiled wire including a proximal segment, a distal segment, and a tissue-engaging tip, the coiled wire having an inner surface, the inner surface being space radially apart from an outer surface of the needle member along a length of the proximal segment, the distal segment extending distally from the proximal segment to the tissue-engaging tip, the distal tip of the needle member being recessed proximally from the tissue-engaging tip by a fixed distance equal to a length of the distal segment, and the coiled wire having a stiffness that prevents deformation of the pitch thereof during operation of the medical access tool wherein the coiled wire is configured to proximally pull tissue up the coiled wire by rotating without advancing until the distal tip passively pierces the tissue without advancing; and a junction connecting the coiled wire to the medical access tool the junction being configured to prevent movement of the coiled wire along the longitudinal axis of the assembly relative to the needle member;

wherein the length of the distal segment of the coiled wire is approximately 0.15 inch, and the coiled wire completes a full revolution along the distal segment.

6. An assembly for a medical access tool, the assembly comprising; a needle member including a proximal end, a piercing distal tip, and a lumen, the needle member extending along a longitudinal axis of the assembly between the proximal end thereof and the piercing distal tip thereof, the lumen extending from a proximal opening thereof at the proximal end to a distal opening thereof at the distal tip, the proximal end being configured to engage with, and disengage from a connector of a syringe assembly, such that the lumen is in fluid communication with an interior of a barrel of the syringe assembly, when the proximal end is engaged therewith;

a coiled wire extending around the longitudinal axis of the assembly with a pitch, the coiled wire including a proximal segment, a distal segment, and a tissue-engaging tip, the coiled wire having an inner surface, the inner surface being spaced radially apart from an outer surface of the needle member along a length of the proximal segment, the distal segment extending distally from the proximal segment to the tissue-engaging tip, the distal tip of the needle member being recessed proximally from the tissue-engaging tip by a fixed distance equal to a length of the distal segment, and the coiled wire having a stiffness that prevents deformation of the pitch thereof during operation of the medical access tool wherein the coiled wire is configured to proximally pull tissue up the coiled wire by rotating without advancing until the distal tip passively pierces the tissue without advancing; and a junction connecting the coiled wire to the medical access tool, the junction being configured to prevent movement of the coiled wire along the longitudinal axis of the assembly relative to the needle member;

wherein the junction connecting the coiled wire comprises a collar mounted around the proximal end of the needle member.

7. A medical. access tool comprising;

a needle member including a proximal end, a piercing distal tip, and a lumen, the needle member extending along a longitudinal axis of the medical access tool between the proximal end thereof and the piercing distal tip thereof the lumen extending from a proximal opening thereof at the proximal end to a distal opening thereof of the distal tip;

a coiled wire extending around the longitudinal axis of the medical access tool with a pitch, the coiled wire including a proximal segment, a distal segment, and a tissue-engaging tip, the coiled wire having an inner surface, the inner surface being spaced radially apart from an outer surface of the needle member along a length of the proximal segment, the distal segment extending distally from the proximal segment to the tissue-engaging tip, the distal tip of the needle member being recessed proximally from the tissue-engaging tip by a fixed distance equal to a length of the distal segment, and the coiled wire having a stiffness that prevents significant deformation. of the pitch thereof during operation of the medical access tool, wherein the coiled wire is configured to proximally pull tissue up the coiled wire by rotating without advancing until the distal tip passively pierces the tissue without advancing; and a junction connecting the coiled wire to the medical access tool, the junction being configured to prevent movement of the coiled wire along the longitudinal axis of the medical access tool relative to the needle members;

wherein the length of the distal segment is approximately 3.81 millimeters.

\* \* \* \* \*